US009709535B2

(12) United States Patent
Michienzi et al.

(10) Patent No.: US 9,709,535 B2
(45) Date of Patent: Jul. 18, 2017

(54) MICROFLUIDIC DEVICE WITH DRIED BLOOD SPOTS (DBS) CARD INTERFACE

(75) Inventors: Joseph D. Michienzi, Plainville, MA (US); James P. Murphy, Franklin, MA (US); Russell L. Keene, Sudbury, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 359 days.

(21) Appl. No.: 14/238,038

(22) PCT Filed: Aug. 22, 2012

(86) PCT No.: PCT/US2012/051876
§ 371 (c)(1),
(2), (4) Date: Feb. 10, 2014

(87) PCT Pub. No.: WO2013/028765
PCT Pub. Date: Feb. 28, 2013

(65) Prior Publication Data
US 2014/0174160 A1    Jun. 26, 2014

Related U.S. Application Data

(60) Provisional application No. 61/525,963, filed on Aug. 22, 2011, provisional application No. 61/525,970, filed on Aug. 22, 2011.

(51) Int. Cl.
G01N 1/00        (2006.01)
G01N 30/06       (2006.01)
(Continued)

(52) U.S. Cl.
CPC ........ G01N 30/06 (2013.01); B01L 3/502715 (2013.01); G01N 30/16 (2013.01);
(Continued)

(58) Field of Classification Search
CPC ........ G01N 30/06; G01N 30/16; G01N 30/88; B01L 2300/0816; B01L 2300/0874
(Continued)

(56) References Cited

U.S. PATENT DOCUMENTS 5,500,071 A * 3/1996 Kaltenbach ....... B01L 3/502707
156/257
5,571,410 A * 11/1996 Swedberg ......... B01L 3/502707
204/451
(Continued)

FOREIGN PATENT DOCUMENTS

EP         2330402      6/2011
JP       2002524755     8/2002
(Continued)

OTHER PUBLICATIONS

Extended Search Report in counterpart European Patent Application No. 12825812.6, mailed Mar. 24, 2015; 7 pages.
(Continued)

Primary Examiner — John Fitzgerald
Assistant Examiner — Rodney T Frank
(74) Attorney, Agent, or Firm — Schmeiser, Olsen & Watts LLP

(57) ABSTRACT

An apparatus for use in a chromatography system includes a first microfluidic substrate having a first fluidic channel. One end of the first fluidic channel terminates at a first fluidic port on a first side of the first microfluidic substrate and an opposite end of the first fluidic channel terminates at a second fluidic port on a second side of the first microfluidic substrate. A second microfluidic substrate has a second fluidic channel. One end of the second fluidic channel terminates at a first fluidic port on a first side of the second microfluidic substrate. The first side of the second microfluidic substrate abuts the second side of the first microflu-
(Continued)

idic substrate such that the fluidic port of the second microfluidic substrate aligns with one of the fluidic ports of the first microfluidic substrate and the alignment produces a fluidic path comprised of the first and second fluidic channels.

29 Claims, 8 Drawing Sheets

(51) Int. Cl.
  *G01N 30/16* (2006.01)
  *B01L 3/00* (2006.01)
  *G01N 30/88* (2006.01)
  *G01N 33/49* (2006.01)
  *G01N 30/60* (2006.01)
  *G01N 30/00* (2006.01)
  *G01N 1/38* (2006.01)

(52) U.S. Cl.
  CPC .............. *G01N 30/88* (2013.01); *G01N 33/49* (2013.01); *B01L 2300/0816* (2013.01); *B01L 2300/0874* (2013.01); *B01L 2300/0887* (2013.01); *B01L 2300/1827* (2013.01); *G01N 30/6095* (2013.01); *G01N 2001/383* (2013.01); *G01N 2030/009* (2013.01); *G01N 2030/062* (2013.01)

(58) Field of Classification Search
  USPC ..... 73/61.55, 61.52, 61.56, 61.58; 422/68.1; 436/161
  See application file for complete search history.

(56) References Cited

U.S. PATENT DOCUMENTS

| | | | | |
|---|---|---|---|---|
| 5,658,413 | A * | 8/1997 | Kaltenbach | B01L 3/502707 156/272.8 |
| 5,997,708 | A * | 12/1999 | Craig | B01L 3/502707 204/601 |
| 6,240,790 | B1 | 6/2001 | Swedberg et al. | |
| 6,303,389 | B1 * | 10/2001 | Levin | B01L 3/50255 422/424 |
| 6,632,399 | B1 * | 10/2003 | Kellogg | B01F 13/0059 422/505 |
| 7,028,536 | B2 * | 4/2006 | Karp | B01L 3/502715 73/61.52 |
| 7,261,812 | B1 | 8/2007 | Karp et al. | |
| 7,811,452 | B2 | 10/2010 | Yin et al. | |
| 7,955,863 | B2 | 6/2011 | Cox | |
| 8,304,230 | B2 * | 11/2012 | Toner | B01L 3/502746 422/414 |
| 8,753,868 | B2 * | 6/2014 | Duthie | C12M 23/16 204/450 |
| 8,940,147 | B1 * | 1/2015 | Bartsch | G01N 27/44791 204/601 |
| 2002/0155032 | A1 | 10/2002 | Liu et al. | |
| 2005/0037484 | A1 | 2/2005 | Staimer et al. | |
| 2010/0171055 | A1 * | 7/2010 | Dourdeville | B23K 20/023 251/129.11 |
| 2010/0210008 | A1 | 8/2010 | Strand et al. | |
| 2010/0213063 | A1 | 8/2010 | Zenhausern et al. | |
| 2011/0053289 | A1 * | 3/2011 | Lowe | B01L 3/5027 436/501 |
| 2011/0107822 | A1 | 5/2011 | Bunner et al. | |
| 2011/0129940 | A1 | 6/2011 | Gijlers et al. | |
| 2011/0133077 | A1 | 6/2011 | Henion et al. | |
| 2012/0028342 | A1 * | 2/2012 | Ismagilov | B01L 3/502738 435/283.1 |
| 2013/0116597 | A1 | 5/2013 | Rudge et al. | |
| 2013/0164856 | A1 * | 6/2013 | Jebrail | B01L 3/502792 436/86 |

FOREIGN PATENT DOCUMENTS

| | | |
|---|---|---|
| JP | 2004144568 | 5/2004 |
| JP | 2005083510 | 3/2005 |
| JP | 2005509142 | 4/2005 |
| JP | 2010511154 | 4/2010 |
| JP | 2011506922 | 3/2011 |
| WO | 2004101151 | 11/2004 |
| WO | 2006123578 | 11/2006 |
| WO | 2010111265 A1 | 9/2010 |
| WO | 2010138667 | 12/2010 |
| WO | 2011044350 | 4/2011 |
| WO | 2013067520 A1 | 5/2013 |

OTHER PUBLICATIONS

International Preliminary Report on Patentability in counterpart international patent application No. PCT/US12/51876, mailed on Mar. 6, 2014; 7 pages.

International Search Report & Written Opinion in related international patent application No. PCT/US12/51876, mailed on Nov. 5, 2012; 8 pages.

International Search Report & Written Opinion in related international patent application No. PCT/US12/51892, mailed on Nov. 2, 2012; 8 pages.

International Preliminary Report on Patentability in related international patent application No. PCT/US12/51892, mailed on Mar. 6, 2014; 7 pages.

Extended European Search Report in related European Patent Application No. 12826104.7, mailed on May 11, 2015; 3 pages.

Heinig, Kataja, et al., "Sensitive determination of a drug candidate in dried blood spots ysing a TLC-MS interface integrated into a column-switching LC-MS/MS system", Bioanalysis, Future Science, Nov. 2010, pp. 1873-1882, vol. 2.

Abu-Rabie, Paul and Neil Spooner, "Direct Quantitative Bioanalysis of Drugs in Dried Blood Spot Samples Using a Thin-Layer Chromatography Mass Spectrometer Interface", Analytical Chemistry, Dec. 15, 2009, pp. 10275-10284, vol. 81, No. 24.

Miller, John H., et al., "Direct analysis of dried blood spots by in-line desorption combined with high-resolution chromatography and mass spectrometry for quantification of maple syrup urine disease biomarkers leucine and isoleucine", Analytical and Bioanalytical Chemistry, Feb. 18, 2011, pp. 237-244, vol. 400.

Non-Final Office Action in related U.S. Appl. No. 14/237,653, mailed on May 17, 2016; 13 pages.

Notice of Rejection in related Japanese Patent Application No. 2014-527268, mailed on May 24, 2016; 5 pages.

Notice of Rejection in counterpart Japanese Patent Application No. 2014-527264, mailed on Jul. 5, 2016; 10 pages.

Final Office Action in related U.S. Appl. No. 14/238,653, mailed on Oct. 19, 2016; 8 pages.

Non-Final Office Action in related U.S. Appl. No. 14/238,653, mailed on Apr. 20, 2017; 9 pages.

* cited by examiner

MICROFLUIDIC DEVICE WITH DRIED BLOOD SPOTS (DBS) CARD INTERFACE

RELATED APPLICATIONS

This application claims priority to and the benefit of the filing date of U.S. Provisional Application Ser. No. 61/525,963, filed Aug. 22, 2011, titled "Microfluidic Device with DBS Card Interface," and of U.S. Provisional Application Ser. No. 61/525,970, filed Aug. 22, 2011, titled "Analysis of Dried Blood Spot Samples in a Microfluidic System with Dilution of Extracted Samples," the entireties of which applications are incorporated by reference herein.

FIELD OF THE INVENTION

The invention relates generally to chromatography. More specifically, the invention relates to liquid chromatography utilizing multiple microfluidic substrates.

BACKGROUND

Chromatography is a set of techniques for separating a mixture into its constituents. Well-established separation technologies include HPLC (High Performance Liquid Chromatography), UPLC (Ultra Performance Liquid Chromatography), and SFC (Supercritical Fluid Chromatography). HPLC systems use high pressure, ranging traditionally between 1,000 psi (pounds per square inch) to approximately 6,000 psi, to generate the flow required for liquid chromatography in packed columns. In contrast to HPLC, UPLC systems use columns with smaller particulate matter and higher pressures approaching 20,000 psi to deliver the mobile phase. SFC systems use highly compressible mobile phases, which typically employ carbon dioxide ($CO_2$) as a principle component.

In general, in a liquid chromatography (LC) application, a solvent delivery system takes in and delivers a mixture of liquid solvents to an autosampler (also called an injection system or sample manager), where an injected sample awaits the arrival of this mobile phase. The mobile phase carries the sample through an analytical column (also referred to as a separation column). In the analytical column, the mixture of the sample and mobile phase divides into bands depending upon the interaction of the mixture with the stationary phase in the analytical column. A detector, for example, identifies and quantifies these bands as they exit the analytical column.

Proteomic analyses often utilize a trap column for sample enrichment and cleaning prior to separation of the sample in an analytical column. Often, different packing material chemistries are used for the trap and analytical columns; sample components trapped on the trap column may be serially driven from the trap to the analytical column during a gradient-based mobile phase elution process. The components can be initially focused at the head of the analytical column, because of the different chemistry, until the gradient attains a level that drives the sample components from the chemistry of the analytical column. In addition, some chromatography instruments use a microfluidic substrate. Such substrates can ease the handling of small samples and reduce undesirable effects, such as dispersion.

SUMMARY

In one aspect, the invention features a chromatography apparatus comprising a first microfluidic substrate having a first fluidic channel. One end of the first fluidic channel terminates at a first fluidic port on a first side of the first microfluidic substrate and an opposite end of the first fluidic channel terminates at a second fluidic port on a second side of the first microfluidic substrate. A second microfluidic substrate has a second fluidic channel. One end of the second fluidic channel terminates at a first fluidic port on a first side of the second microfluidic substrate. The first side of the second microfluidic substrate abuts the second side of the first microfluidic substrate such that the first fluidic port of the second microfluidic substrate aligns with one of the fluidic ports of the first microfluidic substrate and the alignment produces a fluidic path comprised of the first and second fluidic channels.

In another aspect, the invention features a microfluidic substrate comprising a plurality of spatially separated fluidic channels formed therein. One end of the each fluidic channel terminates at a different first fluidic port on a first side of the microfluidic substrate, and an opposite end of each fluidic channel terminates at a different second fluidic port on an opposite side of the microfluidic substrate.

In still another aspect, the invention features a chromatography apparatus comprising a microfluidic cartridge housing a microfluidic device. The microfluidic device is comprised of a first microfluidic substrate having a first fluidic channel and a second microfluidic substrate having a second fluidic channel. One end of the first fluidic channel terminates at a first fluidic port on a first side of the first microfluidic substrate and an opposite end of the first fluidic channel terminates at a second fluidic port on a second side of the first microfluidic substrate. One end of the second fluidic channel of the second microfluidic substrate terminates at a first fluidic port on a first side of the second microfluidic substrate. The first side of the second microfluidic substrate abuts the second side of the first microfluidic substrate such that the first fluidic port of the second microfluidic substrate aligns with one of the fluidic ports of the first microfluidic substrate and the alignment produces a fluidic path comprised of the first and second fluidic channels.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

DETAILED DESCRIPTION

Figure 1:
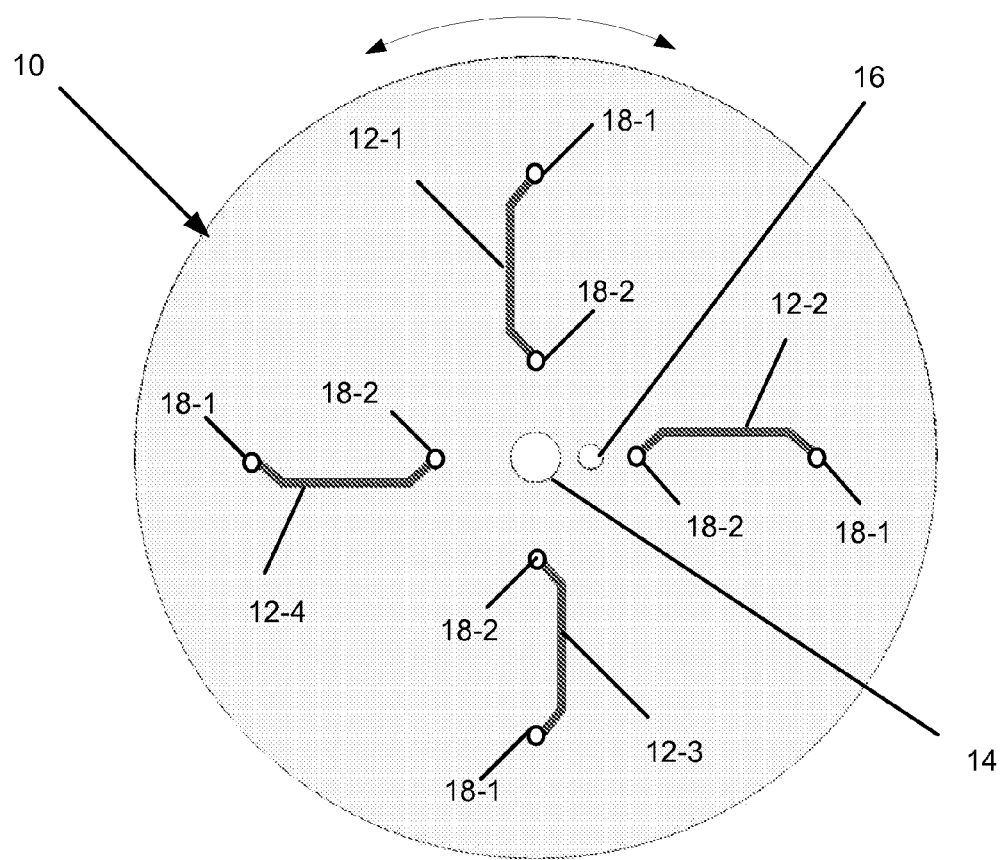
FIG. 1 is a diagram of an embodiment of a disc-shaped microfluidic substrate having formed therein a plurality of channels arranged to accommodate rotary indexing from channel to channel.

Liquid chromatography systems described herein, such as HPLC, UPLC, and SFC systems, employ microfluidic devices comprised of multiple separable microfluidic substrates (or tiles) to provide on-line or off-line sample preparation and on-line sample analysis.

A first one of the multiple microfluidic substrates can have one or more trapping columns, or enhancement columns formed therein. Trapping and enhancement columns preferably contain packing material with chemistries targeted to clean or prepare a sample before analysis. Solid-phase extraction (SPE) processes, for example, commonly use trapping/enhancement columns. As used herein, a reference to a "sample-preparation" column broadly encompasses guard, trapping, and enhancement columns. Another of the multiple microfluidic substrates can have one or more analytical columns or infusion columns for use in conjunction with one or more of the trapping/enhancement tiles. An analytical column preferably contains packing material with chemistries specifically designed to separate a sample into its constituents. Infusion is used, for example, for delivery of a "neat" sample, without separation, to a mass spectrometer. Sample infusions are used, for example, to provide a relatively long analysis of a uniform sample. For example, a sample fraction can be infused for more than 30 minutes, allowing time for various mass spectroscopy (MS) experiments, such as MS/MS, precursor ion or neutral loss scans and/or accurate mass measurements, in positive and/or negative mode.

Multi-tile microfluidic devices with one or more trapping/enhancement tiles may interface directly with a collection device, referred to herein as a dried blood spot (DBS) card or as individual dried blood spots, used to hold dried biological samples. The extraction of a biological sample from the collection device can thus occur directly onto a trapping tile in off-line fashion, or on-line in conjunction with sample analysis.

A cartridge assembly can house any of the various embodiments of multi-tile microfluidic devices described herein, to provide an interface for the microfluidic devices to an analytical apparatus or mass spectroscopy (MS) unit, for example, an ACQUITY® or TRIZAIC® LC/MS system (available from Waters Corporation, Milford, Mass.).

Advantageously, multi-tile microfluidic devices enable one substrate to remain in the housing of the cartridge assembly, while another substrate, such as a trapping/enhancement tile and/or DBS card, is swapped for analyses of different samples. For example, samples may be loaded on several trapping/enhancement tiles, which are then swapped in and out of a cartridge assembly for sequential analysis. In addition, depending on the sample material, the trapping column of a trapping tile may have a shorter useful life than an analytical column of an analytical tile; thus the trapping tile can be replaced without having to replace the analytical tile. As another advantage, packing a column of an analytical tile separately from packing a column of a trapping tile may be facilitated by having the columns reside in different substrates rather than on the same substrate. In addition, different substrates can optionally be maintained at different temperatures. For example, a temperature differential between a trapping tile and an analytical tile may be more readily controlled if the trapping and analytical columns reside in different substrates than if on the same substrate, especially in those embodiments in which the substrates are formed of ceramic materials having a relatively high thermal conductivity. Further, in some embodiments, one or more of the substrates can have heating and/or cooling features that apply active temperature control to the substrates.

FIG. 1 shows an embodiment of a disc-shaped microfluidic substrate 10 having plurality of identical handlebar-shaped microfluidic channels 12-1, 12-2, 12-3, and 12-4 (generally, 12) arranged radially about a central opening 14, like the four cardinal points of a compass. Adjacent to the center hole 14 is a smaller hole 16, used to mark a particular channel (here, for example, channel 12-1). A marked channel enables tracking of the current indexing position of the channels 12 (i.e., the current location of the hole 16 can be used as a reference point for identifying which channels have already been used). One end of each channel 12 has an ingress fluidic port 18-1 disposed on one side of the tile 10, and the opposite end of each channel 12 has an egress fluidic port 18-2 disposed on the other (opposite) side of the tile 10. The egress fluidic port 18-2 may be through-hole, opening to both sides of the microfluidic substrate 10, for facilitating waste removal and at head column dilution, as described in more detail below. In one embodiment, the thickness of the microfluidic substrate 10 can range from approximately 750 µm to greater than 1 mm, and its diameter can range between approximately 1 and 3 inches. The length of the channels can range between approximately 5 cm and 20 cm long; their inner diameters (IDs) can range between approximately 150 µm to 300 µm (preferably 300 µm).

The microfluidic substrate 10 preferably has a multilayer ceramic-based construction. Each microfluidic channel 12 can pass through one or more of the layers (i.e., the depth of a given channel 12 can extend through multiple layers). In addition, different channels 12 can be formed on different layers (with intervening blank layers) of the microfluidic substrate 10, thus allowing for a 3-dimensional (3D) non-interfering overlap of channels. This 3D stacking of channels can contribute to the compactness of the microfluidic substrate 10.

The microfluidic substrate 10 is adapted to rotate about a central axis passing through the center of the center hole 14 (perpendicular to the plane of the figure). The angles between each pair of adjacent channels 12 are the same. For example, for a microfluidic substrate 10 having four identical channels 12, the angle between each pair of adjacent channels is 90 degrees. The angle for a microfluidic substrate with five identical channels, for example, is 72 degrees.

The microfluidic channels 12 can preferably be used as trapping/enhancement columns. When the performance of a channel 12 currently in use has declined below a satisfactory level, for example, the microfluidic substrate 10 can be indexed (i.e., rotated by one position) to disengage the currently used channel 12 and to bring an adjacent channel 12 into use. Such rotation can be manual or automated.

Figure 2:
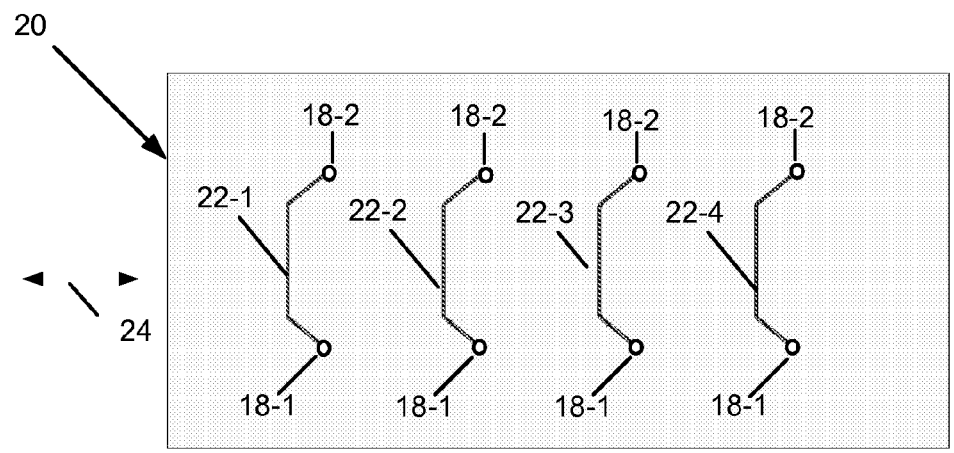
FIG. 2 is a diagram of an embodiment of a card-shaped microfluidic substrate having formed therein a plurality of channels arranged to accommodate linear indexing from channel to channel.

FIG. 2 shows another embodiment of a microfluidic substrate 20 with plurality of identical microfluidic channels 22-1, 22-2, 22-3, and 22-4 (generally, 22) arranged in a row. In one embodiment, the microfluidic substrate 20 is approximately 750 µm to greater than 1 mm in thickness, approximately 3 inches in length, approximately 1 or more inches in width, and the channels 22 have a diameter ranging between approximately 150 µm to 300 µm (preferably 300 µm) and a length ranging between approximately 5 cm and 20 cm.

Similar to the embodiment of FIG. 1, the microfluidic channels 22 can preferably be used as trapping/enhancement columns. For this embodiment, indexing of the microfluidic substrate 20 to change from using one channel 22 to a neighboring channel 22 in the row occurs in a linear direction along the direction signified by the arrow 24. Such linear indexing can be manual or automated.

Figure 3:
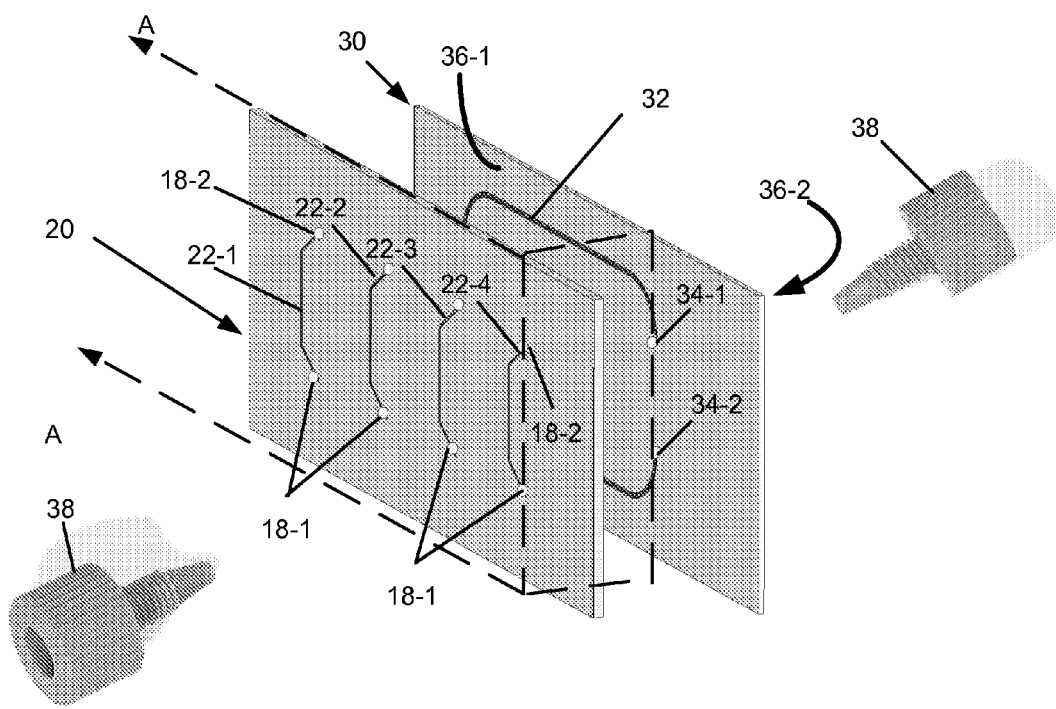
FIG. 3 is a diagram of an embodiment of a first microfluidic substrate, having multiple trapping/enhancement columns, arranged in-line with a second microfluidic substrate, having an analytical column.

FIG. 3 shows a microfluidic device comprised of a first substantially rigid and planar microfluidic substrate 20 of the kind described in FIG. 2, having multiple trapping/enhancement columns 22, arranged in-line with a second substantially rigid and planar microfluidic substrate 30, having, for example, an analytical column 32. In this arrangement, the trapping/enhancement columns 22 and analytical column 32 are on two separate microfluidic substrates. The separate substrates for the trapping/enhancement and analytical columns can be used, for example, for thermal isolation and/or pre-loading of samples. Alternatively, the column 32 on the second microfluidic substrate 30 can be an infusion column.

The analytical column 32 has a fluidic port 34-1 on the inside-facing side 36-1 of the substrate 30 and another fluidic port (in phantom) opening on an outside-facing side 36-2. In this example, the analytical column 32 is an open loop, starting and terminating at the fluidic ports 34-1, 34-2. This shape of the analytical column 32 is just one example. Other embodiments of the analytical column 32 can have a fluidic port that opens at an edge of the substrate 30, instead of opening on the opposite side 36-2. In one embodiment, the analytical column 32 preferably has a 150 µm inner diameter (ID. The diameter of the column 32 preferably ranges between approximately 75 µm and 300 µm (a diameter size of 300 µm may provide increased sensitivity for small molecule and biopharmaceutical analyses in comparison to traditionally larger diameter formats), and the length of the column 32 preferably ranges between 5 cm and 20 cm.

Preferably, the substrates 20, 30 abut each other, back-to-back, with the egress (inside-facing) port 18-2 of the first microfluidic substrate 20 aligning with the fluidic port 34-1 on the inside-facing side 36-1 of the second microfluidic substrate 30. In one embodiment, fluidic nozzles 38 connect to opposite sides of the combined microfluidic device assembly, specifically, to the ingress port 18-1 of the first microfluidic substrate 20 and to the rear-facing port 34-2 of the second microfluidic substrate 30. Tubing (for example, fused silica, stainless steel) connects to these fluidic nozzles 38 for the delivery or extraction of fluid.

Figure 4:
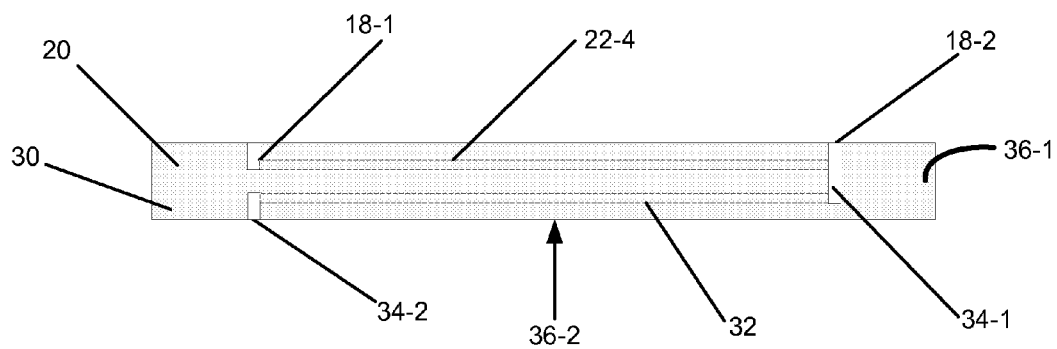
FIG. 4 is a cross-section, taken generally along the line AA in FIG. 3, of the first microfluidic substrate abutting the second microfluidic substrate to provide a fluidic path therebetween.

FIG. 4 shows a cross-section (taken generally along a line like AA in FIG. 3) of the first microfluidic substrate 20 abutting the second microfluidic substrate 30. The cross-section passes through the ports 18-1, 18-2, 34-1, 34-2 of the substrates 20, 30. The egress fluidic port 18-2 of the first microfluidic substrate 20 aligns and makes a fluidic connection with the inside-facing fluidic port 34-1 of the second microfluidic substrate 30.

To accommodate the high fluidic pressures of some chromatography systems in which the microfluidic device may be deployed, without leakage, a variety of features can be implemented. Mechanical fittings (not shown) with a coupling component can be used to hold the substrates 20, 30 together. Fluidic couplers can join aligned fluidic ports of the two microfluidic substrates. Such couplers can have a lumen or channel for passing fluid from the trap tile 20 to the analytical tile 30. Alignment markers, guides, or other such features can facilitate alignment between the substrates 20, 30 to achieve a precise alignment between the ports 18-2, 34-1. Polyimide gaskets can surround the fluidic ports 18, 34 and facilitate sealing between those ports brought into intimate contact. In addition, a microfluidic cartridge assembly used to house the microfluidic device (and interface the device to an analytical apparatus) can have features that guide the alignment and urge the substrates 20, 30 together. Further, a clamping mechanism can apply a mechanical force to one side of the microfluidic cartridge assembly that houses the microfluidic device, urging the substrates together against a "hard stop".

Figure 5:
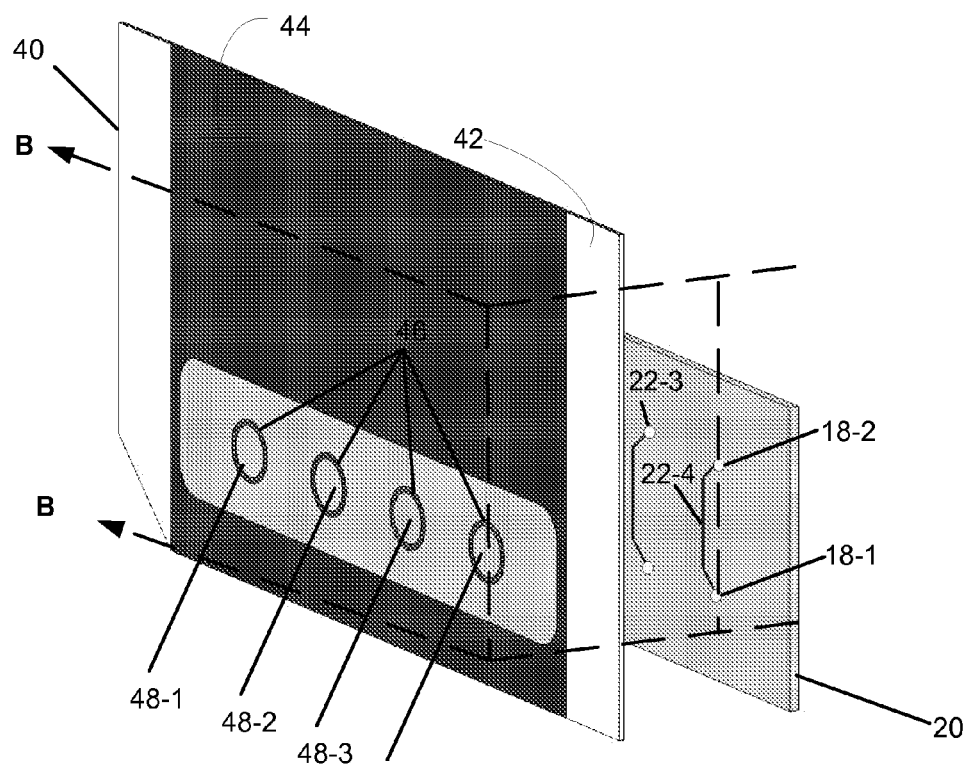
FIG. 5 is a diagram of an embodiment of a collection device, referred to as a DBS (dried blood spot) card, aligned for coupling to a first microfluidic substrate having multiple trapping/enhancement columns

FIG. 5 shows an embodiment of a planar collection device 40 aligned for coupling to a first microfluidic substrate 20 of the kind shown in FIG. 2 having multiple trapping/enhancement columns 22 (of which columns 22-3 and 22-4 are visible). The planar collection device 40 may be referred to as a DBS (dried blood spot) card 40 without any implicit limitation to the types of biological fluids with which the DBS card 40 may be used. The DBS card 40 includes a collection substrate 42 comprised of filter paper or other material capable of absorbing a biological fluid (e.g., blood).

A pattern 44 may be printed into the collection substrate 42 using an ink or other printable substance. In this embodiment, the pattern 44 has a rectangular shape with four circular openings 46. The printable substance fills pores in the filter paper and prevents fluids from being absorbed in the region with the impermeable pattern 44. In some embodiments, a hydrophobic ink is used to produce a pattern 44 that is impermeable to aqueous biological fluids. Examples of the ink or printable substance include, but are not limited to, a wax, a photoresist, a sol-gel precursor, or a polymer precursor. The portions of the collection substrate 42 that are not printed (i.e., the four circular openings 46 in the pattern) are collection regions 48-1, 48-2, 48-3, and 48-4 (generally, 48) for receiving biological fluid samples. The collection regions 48 may be referred to as dried blood spots 48 without any implicit limitation to the types of biological fluids deposited on the spots 48.

In other embodiments, the planar collection device 40 has a paper-based substrate 42 with the impermeable pattern 44 and a number of sample collection regions 48 that function as storage wells. The impermeable pattern 44 is formed in the substrate 42 and can be configured to precisely define the collection volumes, that is, the fluid volume capacities of the sample collection regions 48. In various other embodiments, patterns can include multiple inlet regions or fluidic paths that guide fluid samples to one or more lateral flow filters or other regions of the device. In still another embodiment, the planar collection substrate 42 is a porous thermoplastic material that is heated in one or more defined spatial regions. The heated regions are converted into non-porous and impermeable regions by deformation or melting. The impermeable regions may retain a minor porosity; however, the remaining porosity is insufficient to permit significant infiltration of a fluid sample. This embodiment dispenses with the need to print with an impermeable ink or to apply a non-porous material to the substrate.

The DBS card 40 is aligned with the microfluidic substrate 20 such that at least one of the dried blood spots 48 aligns with an ingress port 18 of one of the trapping/enhancement columns 22. For example, in FIG. 5, the dried blood spot 48-4 is aligned with the ingress port 18-1 of the trapping/enhancement column 22-4. In one embodiment, each dried blood spot 48 aligns with an ingress port 18 of a different one of the trapping/enhancement columns 22. Depending upon the desired application, the multiple trapping/enhancement columns 22 can contain a different resin.

Figure 6:
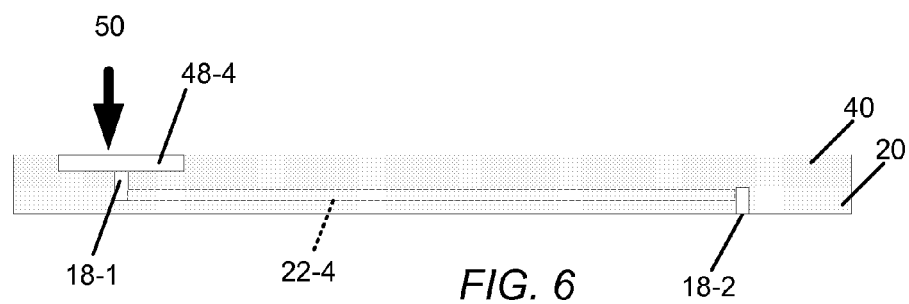
FIG. 6 is a cross-section, taken generally along the line BB in FIG. 5, of the DBS card abutting the first microfluidic substrate to provide a fluidic path for a biological fluid sample extracted from the DBS card.

FIG. 6 shows a cross-section (taken generally along a line like BB in FIG. 5) of the DBS card 40 abutting the microfluidic substrate 20. The cross-section passes through the ports 18-1, 18-2 of the fluidic channel 22-4 in the microfluidic substrate 20 and through the dried blood spot 48-4. Instead of using a complete DBS card 40, dried blood spots 48 can be individually punched out and coupled directly to the microfluidic substrate 20 at the ingress fluidic port 18-1. The extraction principles as applied to the DBS card 40 apply also to individual dried blood spots. During extraction of a biological fluid sample held on the dried blood spot 48-4, the fluid sample is reconstituted by passing an extraction fluid or solvent in the direction of the dashed arrow 50 through the dried sample spot 48-4. In some embodiments, the extraction fluid or solvent is an organic solvent or an aqueous solvent. In another embodiment, the extraction solvent is a supercritical solvent used in a SFC system, for example, supercritical carbon dioxide.

Figure 7:
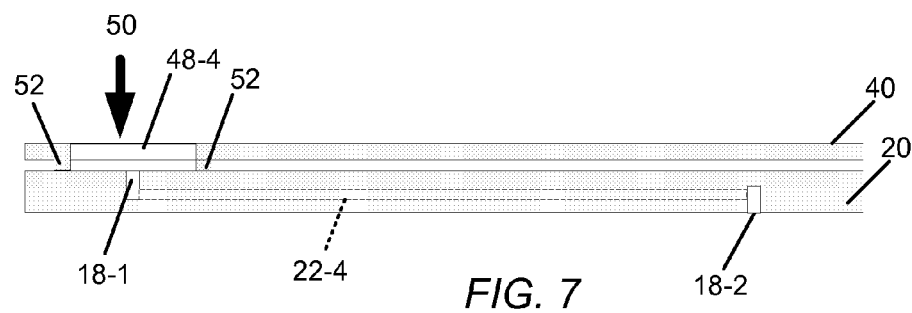
FIG. 7 is another cross-section, taken generally along the line BB in FIG. 5, of the DBS card coupled to the first microfluidic substrate with an intervening leak-proof seal, which provides a fluidic path for a biological fluid sample extracted from the DBS card.

The extracted biological sample flows through the opposite side of the dried sample spot 48-4 into the fluidic port 18-1 of the microfluidic substrate 20 and into the trapping/enhancement column 22-4. A feature of the DBS card 40 can provide a leak-proof seal (e.g., reference numeral 52 of FIG. 7) around the dried blood spot 48-4 that ensures the full volume of reconstituted sample flows into the ingress fluidic port 18-1 of the microfluidic substrate 20. Different mechanisms can be used for extracting the analyte from the dried blood spot without departing from the principles described herein. For example, instead of passing the extraction solvent through the dried blood spot, an extraction device can pass the extraction solvent over the top of the dried blood spot and recover the analyte from the top of the dried blood spot before directing the extracted biological sample into the ingress fluidic port 18-1 of the microfluidic substrate 20.

Figure 8:
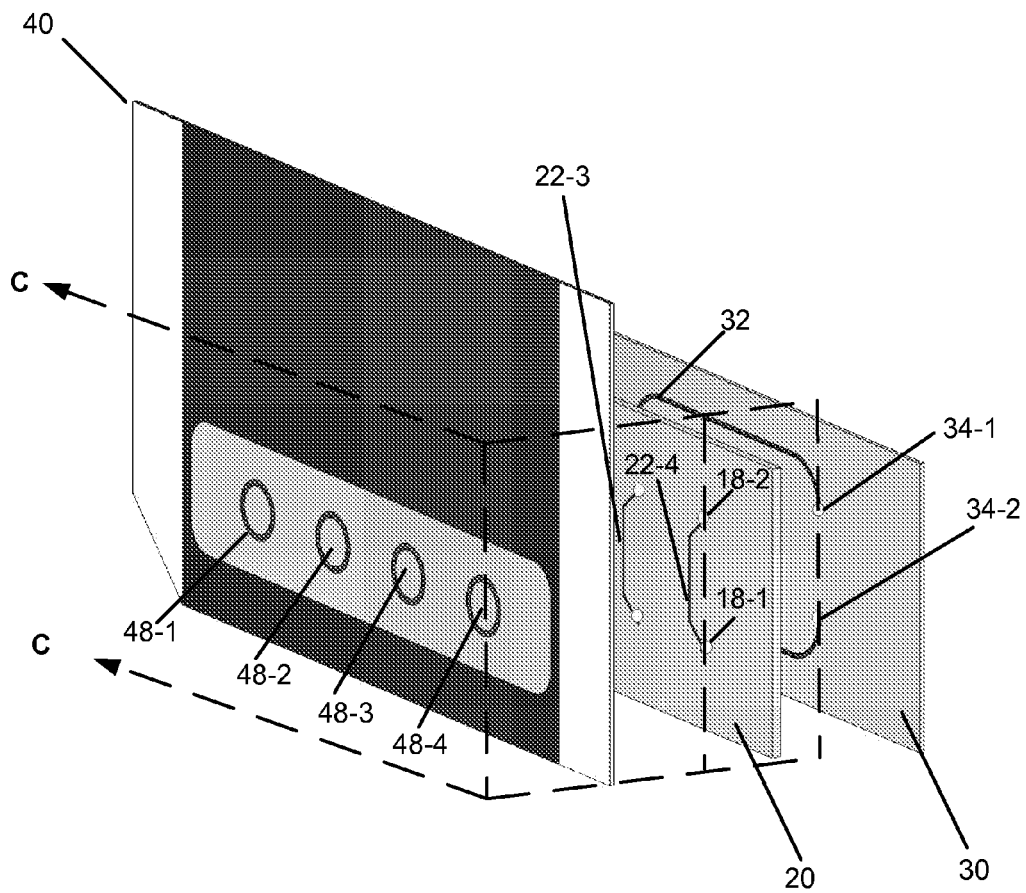
FIG. 8 is a diagram of an embodiment of a DBS card aligned for coupling to a first microfluidic substrate, having multiple trapping columns, arranged in-line with a second microfluidic substrate having, for example, an analytical column.

The extraction achieved with this microfluidic device can occur on-line or off-line. In general, "off-line" preferably means that the microfluidic device for extracting the biological sample may be physically near but unconnected to the process line. An individual uses the microfluidic device to extract a biological sample manually from the DBS card, then carries and introduces the extracted biological sample on the trapping tile to an analytical tile for sample analysis. "On-line" preferably means that the extraction and analysis microfluidic tiles are directly part of a process (or production) line to extract and analyze samples automatically from the process line in approximately real time without manual intervention. The chromatographic analysis can thus occur in parallel to the continued operation of the production/process line. FIG. 8 shows an embodiment of the DBS card 40 aligned to couple to a trapping tile 20 of the kind described in FIG. 2 and arranged in-line with an analytical tile 30 for "on-line" sample extraction and analysis.

Figure 9:
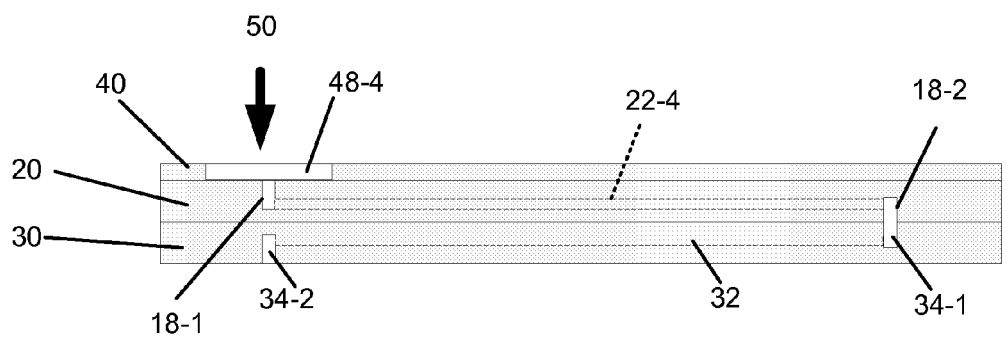
FIG. 9 is a cross-section, taken generally along the line CC in FIG. 8, of the DBS card abutting the first microfluidic substrate, and the first microfluidic substrate abutting the second microfluidic substrate.

FIG. 9 shows a cross-section (taken along a line like the line CC in FIG. 8) of the DBS card 40 abutting the trapping tile 20, and of the trapping tile 20 abutting the analytical tile 30. The cross-section passes through the blood spot 48-4, the ports 18-1, 18-2 of the trapping/enhancement column 22-4 in the trapping tile 20, and the ports 34-1, 34-2 of the analytical column 32 in the analytical tile 30. During extraction of a biological fluid sample on the dried blood spot 48-4, the biological sample is reconstituted by passing an extraction fluid or solvent in the direction of the dashed arrow 50 through or over the top of the dried sample spot 48-4.

The extracted reconstituted sample flows into the fluidic port 18-1 of the trapping tile 20, through the trapping/enhancement column 22-4, and out through the fluidic port 18-2. The extracted biological sample then flows into the fluidic port 34-1 of the analytical tile 30, through the analytical column 32, and out through the fluidic port 34-2. Elute from the analytical tile 30 passes to a detector or mass spectrometer system. Again, instead of using a complete DBS card 40, dried blood spots 48 can be individually punched out and coupled directly to the trapping tile 20 (at or near the fluidic port 18-1).

Figure 10:
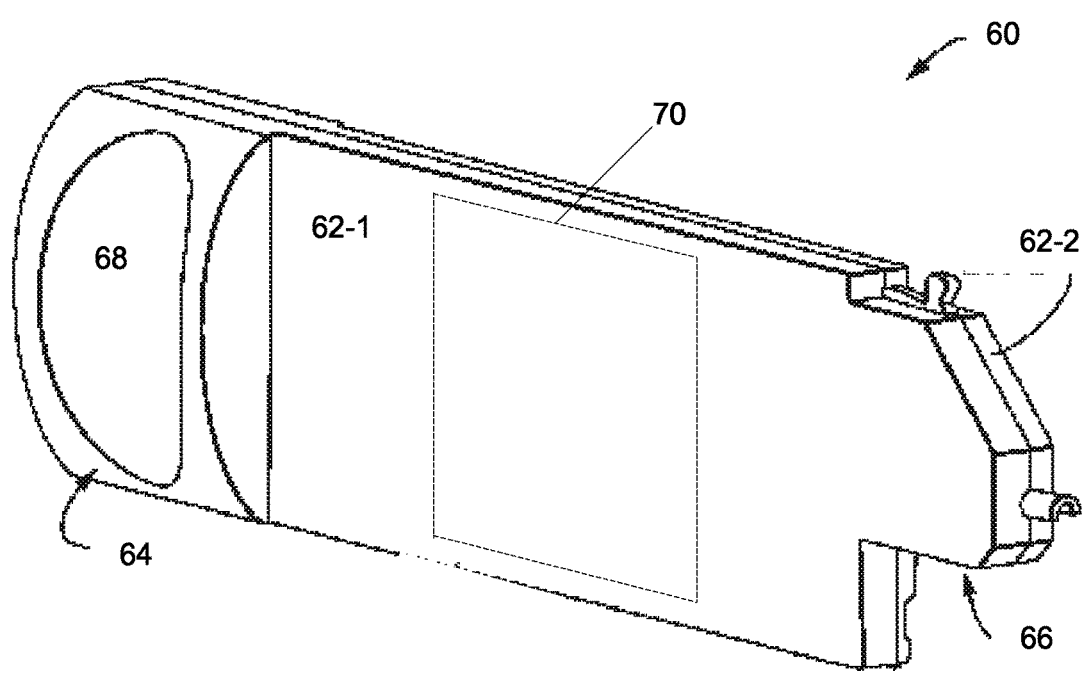
FIG. 10 is a diagram of an embodiment of a microfluidic cartridge assembly for holding multiple microfluidic substrates arranged for on-line processing.

FIG. 10 shows an embodiment of a microfluidic cartridge assembly 60 that can be used to interface the DBS card 40 and microfluidic substrates 20, 30, to a detector, mass spectrometer, or other chromatography apparatus. In brief, this embodiment of the microfluidic cartridge assembly 60 houses an emitter, multiple microfluidic substrates, a heater, and circuitry, and operates as an electromechanical interface for the delivery of voltages, electrical signals, and fluids (gas and liquid) to the various components housed within the microfluidic cartridge assembly 60.

This embodiment of microfluidic cartridge assembly 60 is made by joining two casing sections 62-1, 62-2, for example, by snapping the halves together, or using glue or mechanical fasteners, or any combination thereof. The microfluidic cartridge assembly 60 has a grip end 64 and an emitter end 66. A curved region 68 within the grip end 64 provides a finger hold by which a user can grasp the microfluidic cartridge assembly 60 when coupling it to the chromatography apparatus. One of the casing sections (here, e.g., section 62-1) can have an access panel 70 through which a technician can insert and remove a microfluidic device comprised of a DBS card 40 or an individually punched-out dried blood spot 48, and one or more microfluidic substrates 20, in a manner similar to how a battery is inserted and removed from a mobile phone. The biological sample substrates and microfluidic substrates of the microfluidic device are replaceable because the substrates with the biological sample and trapping/enhancement columns are separate from the microfluidic substrate with the analytical column. Accordingly, the analytical column remains in place with the removal of the DBS card 40, punched-out dried blot spot 48, or of a trapping/enhancement tile 20.

Figure 11:
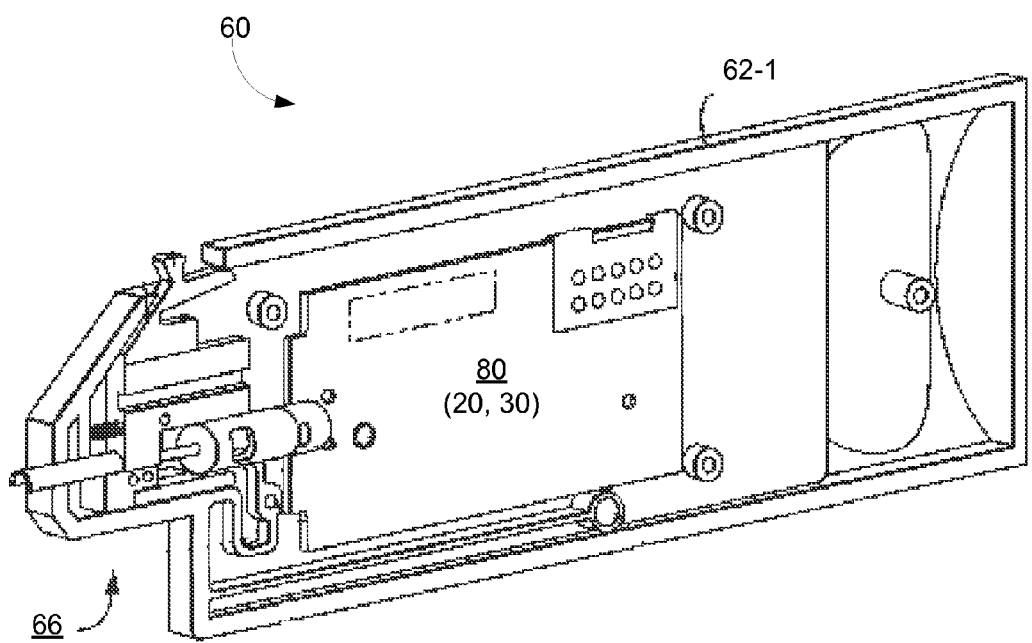
FIG. 11 is a diagram of the microfluidic cartridge assembly with a portion of its housing omitted to show the general location of the microfluidic substrates housed within.

FIG. 11 shows an embodiment of the microfluidic cartridge assembly 60 with the casing section 62-2 omitted to show various components housed within the assembly 60, including the stack 80 of microfluidic substrates 20, 30. The microfluidic cartridge assembly 60 can interface with an autosampler device (not shown) that is configured to index the multi-column trapping tile 20 and DBS card 40 automatically within the assembly 60. Manual indexing can also be implemented.

Various embodiments of microfluidic cartridge assemblies, such as the example described above, can be implemented with any suitable analytical apparatus. For example, some embodiments entail modified liquid-chromatography and/or mass-spectrometry apparatus, for example, an ACQUITY® or TRIZAIC® LC/MS system (available from Waters Corporation, Milford, Mass.)

Figure 12:
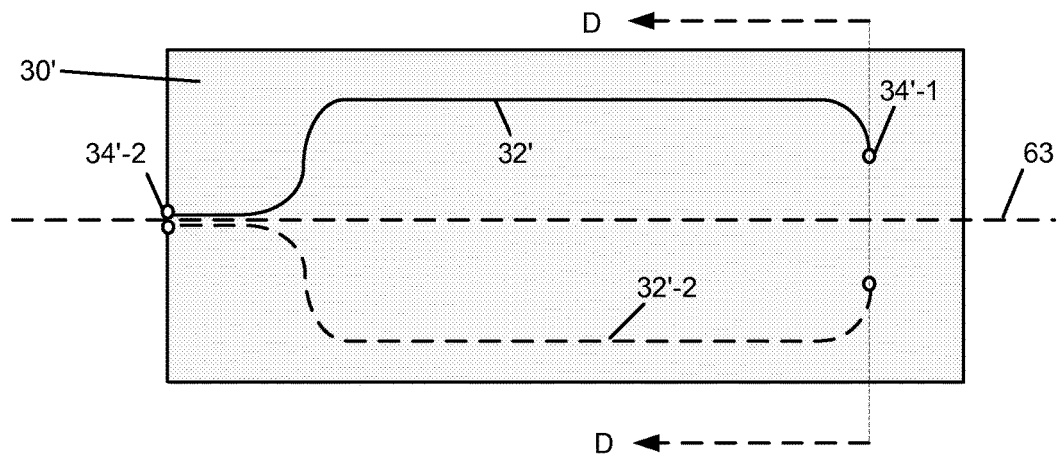
FIG. 12 is a diagram of another embodiment of a microfluidic substrate that can be interfaced to a DBS card, a dried blood spot, and other microfluidic substrates within the microfluidic cartridge assembly.

FIG. 12 shows another embodiment of an analytical tile 30' that can be used within the microfluidic cartridge assembly 60 in conjunction with other substrates, for example, a DBS card 40 and a trapping/enhancement tile 20. The analytical tile 30' includes an analytical column 32' with an ingress fluidic port 34'-1 and an egress fluidic port 34'-2. The ingress port 34'-1 is adapted for fluidic communication with an egress fluidic port 18-2 of the separate, abutting trapping/enhancement tile 20. The ingress fluidic port 34'-1 is a through-hole port that opens on both sides of the microfluidic substrate 30', and can be coupled to a fluidic nozzle and tubing, to allow head-of the-column dilution of an incoming sample (as may be desired for a reversed phase chromatography process). For instance, to enable retention on a reverse phase column, dilution with water may be necessary for an extracted biological sample with a high amount of organic solvent. Through the fluidic nozzle and tubing, a dilution pump can pump a solvent (e.g., water) into the ingress fluidic port 34'-1. Because the fluidic port 34'-1 is at the head of the analytical column 32', the solvent operates to dilute the biological sample before the biological sample enters the analytical column 32'.

The egress fluidic port 34'-2 opens at the edge of the analytical tile 30'. This edge faces the emitter end 66 of the microfluidic cartridge assembly 60 of FIG. 11. The analytical tile 30' can optionally include another (mirror image) analytical column 32' to allow the analytical tile 30' to be installed in the cartridge assembly 60 in one of two orientations (i.e., the analytical tile 30' is symmetric about a horizontal axis 63).

Figure 13:
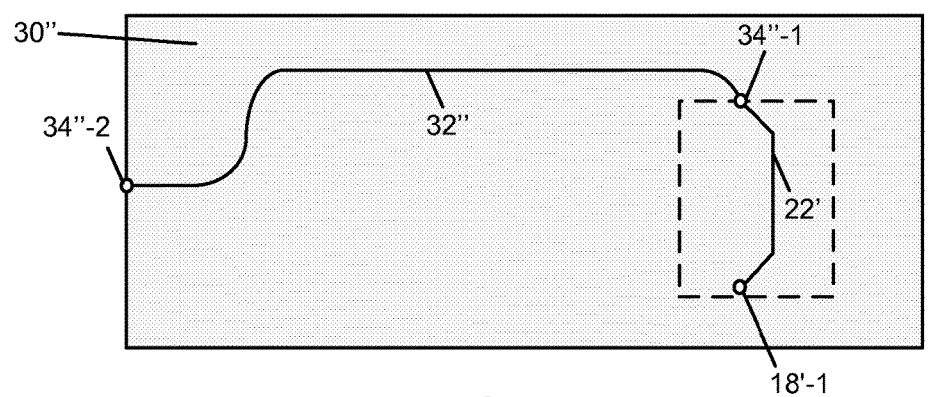
FIG. 13 is a diagram of another embodiment of a microfluidic substrate with an analytical column that can be interfaced to a DBS card or a dried blood spot within the microfluidic cartridge assembly.

FIG. 13 shows another embodiment of an analytical tile 30" that can be used within the microfluidic cartridge assembly 60 in conjunction with a DBS card 40 or an individual dried blood spot 48. The analytical tile 30" includes a trapping/enhancement column 22' integrated on the same substrate with an analytical column 32".

The analytical column 32" has an ingress fluidic port 34"-1 and an egress fluidic port 34"-2. The ingress fluidic port 34"-1 is a port that opens on one (either) or both sides of the microfluidic substrate 30", and can be coupled to a fluidic nozzle and tube, to allow head-of the-column dilution of a sample (e.g., for a reversed phase chromatography process) arriving from the trapping/enhancement column 22'. A dilution pump can pump a solvent into the ingress fluidic port 34"-1, which operates to dilute the biological sample before the biological sample enters the analytical column 32". The diluted biological sample passes through the analytical column 32", which separates the biological sample into is constituent components. The components exit the analytical column 32", for example, in the form of electrospray delivered to a LC detector or mass spectrometer system.

The integrated trapping/enhancement column 22' includes an ingress fluidic port 18'-1, which can be coupled to a dried blood spot for on-line processing with the analytical tile 30". In one embodiment, the trapping/enhancement column 22' can be configured for solid-phase extraction (SPE) to clean the biological sample in preparation for analysis as is generally known in the art. The trapping/enhancement column 22' merges into the analytical column 32" at the ingress fluidic port 34"-1.

Figure 14:
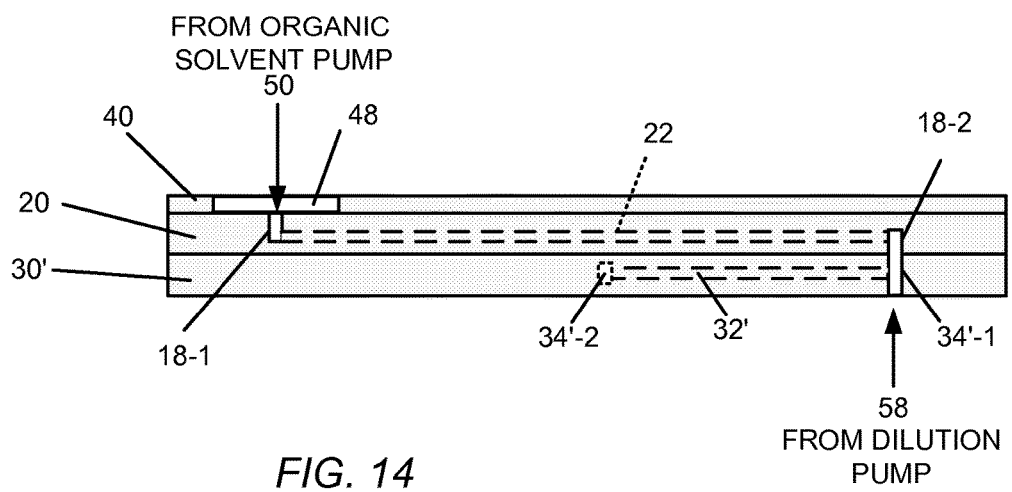
FIG. 14 is a cross-section, taken generally along the line DD in FIG. 12, of the DBS card of FIG. 8 abutting a microfluidic substrate (i.e., trapping/enhancement tile) of FIG. 8, and of a microfluidic substrate abutting the microfluidic substrate (i.e., analytical tile) of FIG. 12.

FIG. 14 shows a cross-section (taken along a line like the line DD in FIG. 12) of the DBS card 40 (FIG. 8) abutting the trapping/enhancement tile 20 (FIG. 2), and of the trapping/enhancement tile 20 abutting the analytical tile 30' of FIG. 12. The cross-section passes through the blood spot 48-4, through the fluidic ports 18-1, 18-2 of the fluidic channel 22 in the trapping/enhancement tile 20, and through the ports 34'-1, 34'-2 of the fluidic channel 32' in the analytical tile 30'.

During extraction of a biological fluid sample on the dried blood spot 48-4, the dried biological sample is reconstituted by passing an extraction fluid or solvent in the direction of the dashed arrow 50 through the dried sample spot 48-4. Again, instead of using a complete DBS card 40, dried blood spots 48 can be individually punched out and coupled directly to the trapping/enhancement tile 20 (at or near the fluidic port 18-1).

The extracted reconstituted sample flows through or over the top of the dried sample spot 48-4 and into the fluidic port 18-1 of the trapping/enhancement tile 20, through the trapping/enhancement column 22-4, and out through the fluidic port 18-2. The extracted biological sample then flows into the fluidic port 34'-1 of the analytical tile 30'.

The fluidic port 34'-1 is at the head of the analytical column 32', and, in one embodiment, is coupled to a dilution pump that pumps a solvent (e.g., water) into the fluidic port 34'-1 in the direction of arrow 58. The solvent operates to dilute the biological sample leaving the trapping/enhancement column 22 before the sample enters the analytical column 32'. The diluted biological sample passes through the analytical column 32', which separates the sample into its constituent components. The components exit the analytical column 32' in the form of an electrospray, for example, directed at a detector or mass spectrometer system.

Figure 15:
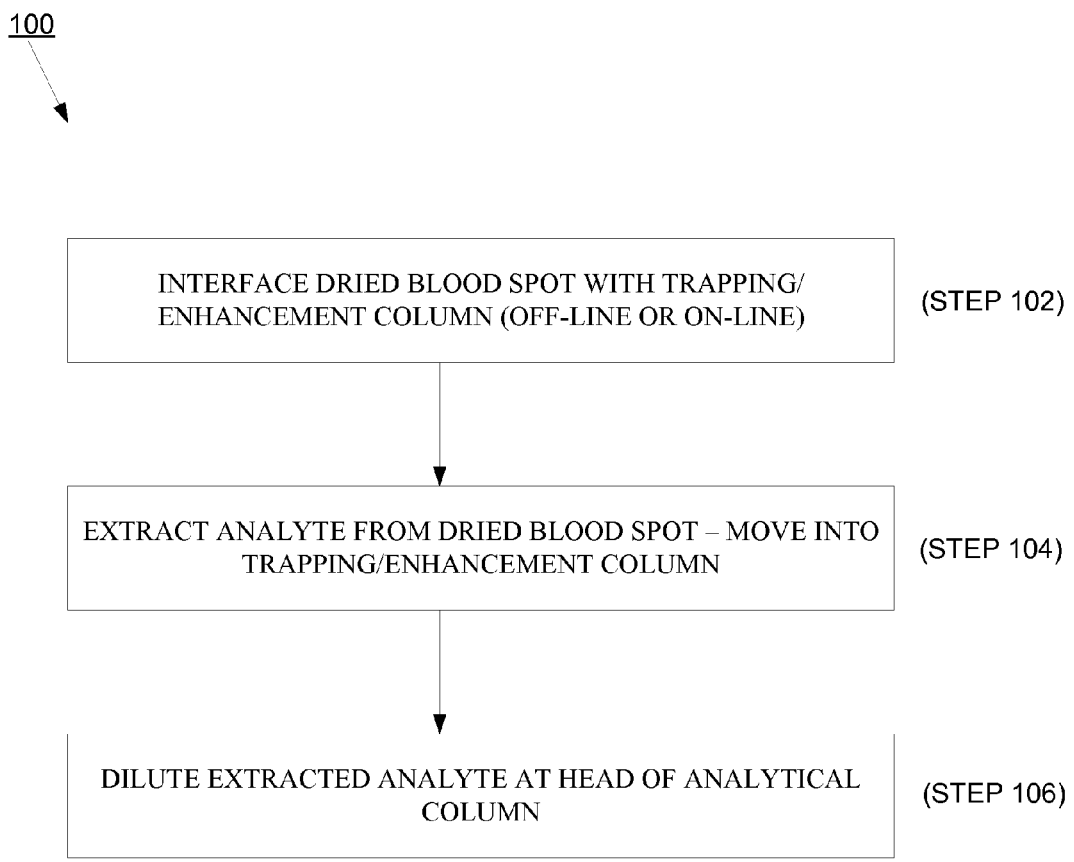
FIG. 15 is a flow diagram of an embodiment of a process for performing a chromatographic analysis of a biological sample deposited on a dried blood spot.

FIG. 15 shows an embodiment of a process 100 for performing a chromatographic analysis of a dried blood spot (e.g., 48-4). At step 102, a dried blood spot (e.g., punched out or part of a DBS card) is interfaced to a microfluidic substrate with a trapping/enhancement column A solvent flows (step 104) over or through the dried blood spot to extract the analyte. The extracted analyte flows into the trapping/enhancement column. The extraction of the analyte can occur off-line, in which instance, the trapping/enhancement tile holding the extracted analyte is carried to and placed in-line with a microfluidic substrate having an analytical column. The extracted analyte is diluted at the head of the analytical column. The analytical column separates the constituent components of the diluted analyte. An electrospray emitter may be fluidically coupled to the egress end of the analytical column for delivering the separated constituents to an LC instrument as an electrospray.

Reference in the specification to "one embodiment" or "an embodiment" means that a particular, feature, structure or characteristic described in connection with the embodiment is included in at least one embodiment of the teaching. References to a particular embodiment within the specification do not all necessarily refer to the same embodiment.

While the invention has been shown and described with reference to specific preferred embodiments, it should be understood by those skilled in the art that various changes in form and detail may be made therein without departing from the spirit and scope of the invention as defined by the following claims.

What is claimed is:

1. A chromatography apparatus comprising:
    a first microfluidic substrate having a first substantially enclosed fluidic channel comprising a sample preparation column, one end of the first substantially enclosed fluidic channel terminating at a first fluidic port on a first side of the first microfluidic substrate and an opposite end of the first substantially enclosed fluidic channel terminating at a second fluidic port on a second side of the first microfluidic substrate;
    a second microfluidic substrate having a second substantially enclosed fluidic channel comprising an analytical column, one end of the second substantially enclosed fluidic channel terminating at a first fluidic port on a first side of the second microfluidic substrate, and
    a dried blood spot (DBS) card having one or more dried blood spots, one side of the DBS card being coupled to the first side of the first microfluidic substrate such that one of the dried blood spots of the DBS card is in fluidic communication with the first fluidic port of the first microfluidic substrate;
    wherein the first side of the second microfluidic substrate abuts the second side of the first microfluidic substrate such that the first fluidic port of the second microfluidic substrate aligns with one of the second fluidic ports of the first microfluidic substrate and the alignment produces a fluidic path comprised of the first and second substantially enclosed fluidic channels.

2. The chromatography apparatus of claim 1, wherein the first microfluidic substrate includes a plurality of substantially enclosed fluidic channels, one end of each substantially enclosed fluidic channel of the first microfluidic substrate terminating at a different first fluidic port on the first side of the first microfluidic substrate and an opposite end of each substantially enclosed fluidic channel of the first microfluidic substrate terminating at a different second fluidic port on the second side of the first microfluidic substrate.

3. The chromatography apparatus of claim 2, wherein the first microfluidic substrate is card-like in shape and the substantially enclosed fluidic channels are arranged in a row for linear indexing.

4. The chromatography apparatus of claim 2, wherein the first microfluidic substrate is disc-like in shape and the substantially enclosed fluidic channels are arranged radially about a center of the first microfluidic substrate for rotary indexing.

5. The chromatography apparatus of claim 2, wherein each of the substantially enclosed fluidic channels of the first microfluidic substrate comprises a sample-preparation column.

6. The chromatography apparatus of claim 2, wherein the DBS card is coupled to the first side of the first microfluidic substrate such that each of the dried blood spots of the DBS card is in fluidic communication with a different first fluidic port on the first side of the first microfluidic substrate.

7. The chromatography apparatus of claim 1, wherein the first microfluidic substrate is removably coupled to the second microfluidic substrate.

8. The chromatography apparatus of claim 1, wherein the first microfluidic substrate is movably coupled to the second microfluidic substrate for indexing.

9. The chromatography apparatus of claim 1, further comprising a fluidic coupler coupled to the first fluidic port on the first side of the first microfluidic substrate and a second fluidic coupler coupled to the second fluidic port on the second side of the second microfluidic substrate.

10. The chromatography apparatus of claim 1, further comprising a third microfluidic substrate having a fluidic channel, one end of the fluidic channel of the third microfluidic substrate terminating at a first fluidic port on a first side of the third microfluidic substrate and an opposite end of the fluidic channel of the third microfluidic substrate terminating at a second fluidic port on a second side of the third microfluidic substrate;
    wherein the second side of the third microfluidic substrate abuts the second side of the first microfluidic substrate such that one of the fluidic ports of the third microfluidic substrate aligns with one of the fluidic ports of the first microfluidic substrate and the alignment produces a fluidic path comprised of the fluidic channels of the first and third microfluidic substrates.

11. The chromatography apparatus of claim 1, wherein the second substantially enclosed fluidic channel of the second microfluidic substrate terminates at a second fluidic port opening to a second side of the second microfluidic substrate.

12. The chromatography apparatus of claim 1, wherein the second substantially enclosed fluidic channel of the second microfluidic substrate terminates at a second fluidic port opening at an edge of the second microfluidic substrate.

13. A chromatography apparatus comprising:
    a first microfluidic substrate comprising a plurality of spatially separated substantially enclosed fluidic channels each comprising a sample preparation column formed therein, one end of each of the substantially enclosed fluidic channels terminating at a different first fluidic port on a first side of the microfluidic substrate, and an opposite end of each substantially enclosed fluidic channel terminating at a different second fluidic port on a second side opposite the first side of the microfluidic substrate, and
    a second microfluidic substrate having a second substantially enclosed fluidic channel comprising an analytical column, one end of the second substantially enclosed fluidic channel terminating at a first fluidic port on a first side of the second microfluidic substrate, and
    wherein the first side of the second microfluidic substrate abuts the second side of the first microfluidic substrate such that the first fluidic port of the second microfluidic substrate aligns with one of the fluidic ports of the first microfluidic substrate and the alignment produces a fluidic path comprised of the first and second substantially enclosed fluidic channels.

14. The chromatography apparatus of claim 13, wherein the first microfluidic substrate is card-like in shape, and the spatially separated substantially enclosed fluidic channels are identical in shape and arranged in a row for linear indexing.

15. The chromatography apparatus of claim 13, wherein the first microfluidic substrate is disc-like in shape, and the spatially separated substantially enclosed fluidic channels are identical in shape and arranged radially about a center of the microfluidic substrate for rotary indexing.

16. The chromatography apparatus of claim 13, wherein each of the sample-preparation columns contain a different resin.

17. The chromatography apparatus of claim 13 further comprising a multilayer construction, wherein one or more of the substantially enclosed fluidic channels cuts through multiple layers of the multilayer construction.

18. The chromatography apparatus of claim 13, further comprising a multilayer construction, wherein different ones of the substantially enclosed fluidic channels are formed in different layers of the multilayer construction.

19. The chromatography apparatus of claim 13, further comprising a dried blood spot (DBS) card having one or more dried blood spots, one side of the DBS card being coupled to the first side of the first microfluidic substrate such that each of the dried blood spots of the DBS card is in fluidic communication with a different first fluidic port on the first side of the first microfluidic substrate.

20. A chromatography apparatus, comprising:
a microfluidic cartridge housing a microfluidic device comprised of:
a first microfluidic substrate having a first substantially enclosed fluidic channel comprising a sample preparation column, one end of the first substantially enclosed fluidic channel terminating at a first fluidic port on a first side of the first microfluidic substrate and an opposite end of the first substantially enclosed fluidic channel terminating at a second fluidic port on a second side of the first microfluidic substrate;
a dried blood spot (DBS) card having one or more dried blood spots, one side of the DBS card being coupled to the first side of the first microfluidic substrate such that one of the dried blood spots of the DBS card is in fluidic communication with the first fluidic port of the first microfluidic substrate; and
a second microfluidic substrate having a second substantially enclosed fluidic channel comprising an analytical column, one end of the second substantially enclosed fluidic channel terminating at a first fluidic port on a first side of the second microfluidic substrate,
wherein the first side of the second microfluidic substrate abuts the second side of the first microfluidic substrate such that the first fluidic port of the second microfluidic substrate aligns with one of the second fluidic ports of the first microfluidic substrate and the alignment produces a fluidic path comprised of the first and second substantially enclosed fluidic channels, and wherein the first microfluidic substrate is removably coupled to the second microfluidic substrate and removable from the cartridge housing.

21. The chromatography apparatus of claim 20, wherein the first microfluidic substrate includes a plurality of substantially enclosed fluidic channels, one end of each substantially enclosed fluidic channel of the first microfluidic substrate terminating at a different first fluidic port on the first side of the first microfluidic substrate and an opposite end of each substantially enclosed fluidic channel of the first microfluidic substrate terminating at a different second fluidic port on the second side of the first microfluidic substrate.

22. The chromatography apparatus of claim 21, wherein the first microfluidic substrate is rectangular in shape and the substantially enclosed fluidic channels are arranged in a row for linear indexing.

23. The chromatography apparatus of claim 21, wherein the first microfluidic substrate is circular in shape and the substantially enclosed fluidic channels are arranged radially about a center of the first microfluidic substrate for rotary indexing.

24. The chromatography apparatus of claim 21, wherein each of the substantially enclosed fluidic channels of the first microfluidic substrate comprises a sample-preparation column.

25. The chromatography apparatus of claim 21, wherein the DBS card is coupled to the first side of the first microfluidic substrate such that each of the dried blood spots of the DBS card is in fluidic communication with a different first fluidic port on the first side of the first microfluidic substrate.

26. The chromatography apparatus of claim 20, wherein the first microfluidic substrate movably coupled to the second microfluidic substrate for indexing within the cartridge housing.

27. The chromatography apparatus of claim 20, further comprising a fluidic coupler coupled to the first fluidic port on the first side of the first microfluidic substrate and a second fluidic coupler coupled to the second fluidic port on the second side of the second microfluidic substrate.

28. The chromatography apparatus of claim 20, wherein the microfluidic device further comprises a third microfluidic substrate having a fluidic channel, one end of the fluidic channel of the third microfluidic substrate terminating at a first fluidic port on a first side of the third microfluidic substrate and an opposite end of the fluidic channel of the third microfluidic substrate terminating at a second fluidic port on a second side of the third microfluidic substrate;
wherein the second side of the third microfluidic substrate abuts the second side of the first microfluidic substrate such that one of the fluidic ports of the third microfluidic substrate aligns with one of the fluidic ports of the first microfluidic substrate and the alignment produces a fluidic path comprised of the fluidic channels of the first and third microfluidic substrates.

29. The chromatography apparatus of claim 20, wherein the second substantially enclosed fluidic channel of the second microfluidic substrate terminates at a second fluidic port opening at an edge of the second microfluidic substrate.

* * * * *